(12) United States Patent
Kaneshika

(10) Patent No.: US 11,680,003 B2
(45) Date of Patent: Jun. 20, 2023

(54) TREATMENT OF ANIMAL AND POULTRY WASTE TO REDUCE ODOR

(71) Applicant: Isao Kaneshika, Hyogo-Prefecture (JP)

(72) Inventor: Isao Kaneshika, Hyogo-Prefecture (JP)

( * ) Notice: Subject to any disclaimer, the term of this patent is extended or adjusted under 35 U.S.C. 154(b) by 275 days.

(21) Appl. No.: 16/814,564

(22) Filed: Mar. 10, 2020

(65) Prior Publication Data

US 2021/0284560 A1    Sep. 16, 2021

(51) Int. Cl.
*C02F 11/02* (2006.01)
*C02F 3/34* (2023.01)
*A01K 1/00* (2006.01)
*C12N 1/20* (2006.01)
*C02F 103/20* (2006.01)

(52) U.S. Cl.
CPC ............ *C02F 11/02* (2013.01); *A01K 1/0094* (2013.01); *C02F 3/345* (2013.01); *C12N 1/20* (2013.01); *C02F 2103/20* (2013.01); *C02F 2303/02* (2013.01)

(58) Field of Classification Search
CPC ..... A61K 35/744; C02F 2303/02; C02F 3/34; C02F 2101/101; C02F 2103/20
USPC .................................................. 210/601, 916
See application file for complete search history.

(56) References Cited

U.S. PATENT DOCUMENTS

| 4,902,431 | A | 2/1990 | Nicholson et al. | |
| 5,707,856 | A * | 1/1998 | Higa | C02F 3/34 435/267 |
| 5,958,758 | A | 9/1999 | Miller et al. | |
| 6,908,554 | B2 * | 6/2005 | Jackson | C02F 11/12 210/801 |
| 2001/0011643 | A1 * | 8/2001 | Newton | C02F 3/10 210/601 |
| 2014/0342437 | A1 * | 11/2014 | Carpenter | C12N 1/20 435/252.4 |

* cited by examiner

*Primary Examiner* — Claire A Norris
(74) *Attorney, Agent, or Firm* — McKee, Voorhees & Sease, PLC

(57) ABSTRACT

Animal and poultry solid waste material are treated with a preferred *lactobacillus* organism, preferably plant derived, in a liquid medium, preferably non-chlorinated water for time sufficient to reduce odor a significant amount.

7 Claims, No Drawings

TREATMENT OF ANIMAL AND POULTRY WASTE TO REDUCE ODOR

FIELD OF THE INVENTION

The present invention relates generally to the treatment of animal wastes generated at facilities where animals such as hogs, cattle, and poultry are raised. More particularly, the invention relates to a microbial process for treating animal waste in waste holding facilities in order to reduce the sulfide, ammonia and mercaptan content and enhance efficient degradation of the waste without significant odor.

BACKGROUND OF THE INVENTION

The treating of an animal and human wastes for various purposes has been taking place for centuries. In modern times, this activity has centered primarily on municipal sewage and waste water treatment plants, and on manure collected at livestock and poultry feeding facilities. Examples of this technology are shown in U.S. Pat. No. 5,958,758.

In the area of animal and poultry wastes, the odor emitted by the manure, has been the primary concern, and while this matter has been addressed (e.g. U.S. Pat. No. 4,902,431), no universally acceptable manure odor reduction processes have been developed to effectively combat this problem.

Animal and poultry wastes appear in different locations and different holding devices in a multitude of animal and poultry confinement buildings which have emerged in great numbers over the last 50 years. These facilities include slotted floors and solid floors from which manures are collected by manual or mechanical scraping or flushing; gutters; recirculation flush pits; and gravity flow channels. They also include open feed lots utilizing paved or earthen surfaces with runoff channels of varying designs. Liquid-solid separation systems include settling tanks, basins, channels, mechanical separation systems, evaporation ponds and dehydrators. Liquid manure storage systems utilize manure pits, earthen storage basins (i.e., lagoons), and aboveground tanks.

It is therefore a primary object of the present invention to provide a method of reducing odors in manure, particularly animal and poultry manure namely pigs, cattle, chickens and turkey. Wherein the manure is comprised of liquids and solids.

A further object is to provide a process of odor reduction in the manure which can be sustained and maintained at a lower odor level with diluted treatments for the treating material.

A still further objective is to treat manure odors with an all-natural treating composition comprising lactic acid bacteria as the primary active component of the treating medium.

These and other objects will become apparent to those skilled in the art for the following description of the invention.

SUMMARY OF THE INVENTION

The present invention provides a process for treatment of large amounts of animal and poultry waste which often accompany hog and turkey growth plants. The process provides an appropriate *lactobacillus*-based treatment medium of naturally occurring materials, preferably plant derived which when applied reduce odors caused by sulfides, ammonia, volatile fatty acids, mercaptans, etc. Once initial odor is reduced, they can be continually treated at diluted levels to sustain odor reduction. The preferred treatment method is spraying a liquid medium, preferably non-chlorinated water based.

DETAILED DESCRIPTION OF INVENTION

A preferred process of the present invention involves spraying a liquid medium containing *lactobacillus* organisms. The material is sprayed on top of the waste manure. Initially the bacteria used in the spray can be active bacteria in a dry powder form, and in a liquid suspension, in a salt or gel or any other convenient dispensable medium. The preferred medium is however non chlorinated water for a variety of reasons. One it does not interact with and react with the waste. Secondly it is cheap, third it readily solubilizes any dried active bacteria form.

Lactic acid bacteria are the general term for bacteria which generate lactic acid by metabolism. They contribute to the fermentation of food: such as yogurt, miso or fermented soybean paste, and pickles. 100 trillion or more of them exist in a person's intestines, and are also known for functions such as digestion, nutrient absorption, and hygiene management.

Lactic acid bacteria were discovered by the French scientist, Louis Pasteur, and were defined by Sigurd Orla-Jensen. According to them, lactic acid bacteria produce a lot of lactic acid, and propagate well in a culture medium containing carbohydrates, and they are gram-positive, immotile, and do not build spores.

Moreover, to glucose, lactic acid bacteria produce lactic acid following the first fermentation formula (Homo fermentation formula=only lactic acid is generated) or the second fermentation formula (Hetero fermentation formula=acetic acid, alcohol, etc. other than lactic acid are generated), and do not produce catalase.

They have 15 bacteriological genera, and the typical ones are the following 6.

*Lactobacillus*

It is a gram-positive *bacillus*. Some produce only lactic acid (Homo fermentation). The others produce not only lactic acid but also other substances (Hetero fermentation). *L. delbrueckii, L. acidophilus, L. casei*, etc.

*Lactobacillus* are easily dissociated from natural sources and have been used to make yogurt since antiquity. Such bacteria live in the alimentary canal of humans and animals, and is easily dissociated from their feces and urine. The bacteria group called *Döderlein bacillus* which lives in the vagina also mainly consists of *Lactobacillus*.

Moreover, some genera such as *L. fructivorans, L. hilgardii, L. paracasei*, and *L. rhamnosus*, are not much affected by alcohol. They are called "hiochi bacteria" in Japanese sake brewing, and mixing this *bacillus* causes the development of bad odors or acidity, etc. in sake (hiochi). However, *L. paracasei* and *L. plantarum* perform malolactic fermentation of wine.

*Bifidobacterium*

*Bifidobacterium* is a gram-positive obligate anaerobic *bacillus*, and often shows the branched forms such as V shaped or Y shaped at the time of proliferation.

It is also commonly called a *bifidus* bacterium, and is a kind of hetero lactic acid bacteria, producing lactic acid and acetic acid. *B. bifidum, B. adolescentisetc.*

The bacterium of *Bifidobacterium* genus, an alimentary canal living bacterium, can be seen most in a maternal feeding baby's alimentary canal. It is replaced by other anaerobic bacterium as they grow up.

*Enterococcus*

*Enterococcus* is a gram-positive *micrococcus*, performing Homo fermentation, and inhabiting the ileum, the cecum, and the large intestine. *E. faecalis, E. faecium*, etc. is used in medicine for controlling intestinal functions, which contains three bacteria: *Bifidobacterium, Lactobacillus, Enterococcus*. Also the immunity activation capability of a fungal body whose *E. faecalis* EF-2001 is sterilized by heat.

*Lactococcus*

*Lactococcus* is a gram-positive *micrococcus*, takes the arrangement of a chain or a diplococcus, and performs Homo fermentation. It exists in many milk or dairy products, and is used in fermented milk products whose ingredients are milk or dairy products. *L. lactis, L. cremoris*, etc.

*Pediococcus*

*Pediococcus* is a gram-positive *micrococcus* and takes the arrangement of *pediococcus*. It performs Homo fermentation, and is often dissociated from fermented vegetable products, such as pickles. *P. damnosus* etc.

*Leuconostoc*

*Leuconostoc* is a gram-positive *micrococcus*, and takes the arrangement of a chain or a diplococcus. It performs Hetero fermentation, and is often dissociated from fermented vegetable products, such as sauerkraut. *L. mesenteroides*, etc. *L. mesenteroides* performs the Malolactic fermentation of wine.

The lactic acid bacteria preferred are a mixture, mainly consisting of *Lactobacillus* containing other bacteria. It can be shipped in a liquid medium at a normal temperature.

The preferred lactic acid bacteria are bacteria of plant origin.

The lactic acid bacteria currently preferred are extracted from plants and then cultivated. They are supposed to be stronger in severe environments compared to the lactic acid bacteria which live in specific environments. Most preferred are bacteria containing x a lot of species that are especially excellent in acid proofing and salt-resisting.

They are bacteria which exist in nature.

They are not the lactic acid bacteria developed and engineered in order to be added into health food etc. but bacteria already thriving in nature, which are cultivated and proliferated without additives. Therefore, they do not influence the natural balance or the activity of other fermentative bacteria. Moreover, since they are the same bacteria as in fermented foods manufactured traditionally such as pickles and fermented soybean paste, there is less risk of adverse health effects on animals as well as human beings. (They are not for drinking but are thought to promote health by drinking them.)

No chemical products, chemicals, additives, or preservatives are used at all when these lactic acid bacteria are extracted and cultivated. No heat treatment is applied at all, either.

They are live bacteria, preferably not in an inactive state.

As they keep generating at 4 or less-PH lactic acid, they can be widely used for the purpose of an environmental program, and the effects appear immediately by spraying or injecting them. These lactic acid bacteria can be used for about 20 days even when they are left at a normal temperature without any special treatment.

Ideally, they are bacteria in the fermentative-bacteria group present.

Since bacteria extracted from plants are used without sorting out, not merely lactic acid bacteria but a group of fermentative bacteria are provided, which are compatible with the lactic acid bacteria, such as photosynthesis bacteria, yeast fungus, ray fungus, and acetic acid bacteria. These contain a lot which have good influences on health and the environment.

It is preferred that the lactic acid are bacteria selected from lactic acid bacteria derived from plants (leafy vegetables such as lettuce, spinach and cabbage are good examples) are alive and, particularly when derived from plants will typically contained some carbohydrates, some salts as well as water. Salts typically are nitrates, salts of magnesium, salts of sodium and are diluted with water until the medium should contain lactic acid bacteria at a concentration of about at least $10 \times 10^6$ Cfu/gm. Overall the lactic salts of potassium and the carbohydrates are present at about 1.2% by weight but may be within the range of from 1.0% to 1.07 by weight or more if desired.

The undiluted bacterium and medium could be added to the waste material whose odor is to be reduced at a range of about 3% to 10% by weight of the waste material, preferably at about 5% by weight of the waste material. Preferably the temperature should be at least 10° C. to make sure the bacteria are active.

After the first reduction of odor occurs one may continue to keep the odor down by use of about a 1-4 dilution of the original material sprayed on at 5% at various intervals, say once per day.

Example

The following example is offered to illustrate but not limit the process of the present invention. Table 1 shows the parts per million test of ammonia hydrogen sulfide dimethyl sulfide at the beginning. Treatment continued daily until the odor was noticeably reduced at which point the ammonia and the hydrogen sulfide dimethyl sulfide as per million were again tested with the result shown in Table 2. Spraying is the preferred method of addition.

TABLE I

| No. | Analyte | Result | Unit |
| --- | --- | --- | --- |
| 1 | ammonia | 0.51 | ppm |
| 2 | hydrogen sulfide | 0.49 | ppm |
| 3 | dimethyl sulfide | 0.19 | ppm |

As can be seen the ammonia went from 0.51 ppm to 0.20 ppm a 39% reduction. Hydrogen sulfide went from 0.49 to 0.28 showing a 57% reduction. The dimethyl sulfide went from 0.019 to 0.0009 showing an almost complete reduction.

TABLE II

| No. | Analyte | Result | Unit |
| --- | --- | --- | --- |
| 1 | ammonia | 0.20 | ppm |
| 2 | hydrogen sulfide | 0.28 | ppm |
| 3 | dimethyl sulfide | <0.0009 | ppm |

The procedure was as follows. The specimen (animal waste) was placed in an air tight container. After one hour, the air above the waste was siphoned off and analyzed for the three (3) chemicals listed in the table. The active bacteria medium (water and lactic acid bacteria) was added, stirred and again sealed for seven days. The room temperature was about 22° C. the amount of test waste was 2 kg. The amount of bacteria medium added was 900 ml with approximately 28 billion bacteria present.

It can be seen from the above that the process accomplished its objectives. Air quality in a hog barn would be noticeably improved as evidence from the data in the tables.

What is claimed is:

1. A process for treating animal and poultry wastes to reduce odors comprising:
   treating an amount of odor producing animal or poultry waste with a lactic acid bacteria medium, wherein:
   the odors reduced are offensive odors of ammonia, mercaptan, and hydrogen sulfide,
   the lactic acid bacteria are derived from leafy vegetables,
   the lactic acid bacteria medium is a liquid medium which is cultivated without sorting out bacteria derived from the leafy vegetables, and
   the treating is by spraying with the lactic acid bacteria medium containing a lactic acid bacteria concentration of at least $10 \times 10^6$ cfg/gram,
   wherein the spraying is at a rate of about 200 ml of the lactic acid bacteria medium per square meter, at least twice a week.

2. The process of claim 1 wherein the lactic acid bacteria are selected from the group consisting of *Lactobacillus, Bifidobacterium, Enterococcus, Lactococcus, Pediococcus*, and *Leuconostoc*.

3. The process of claim 1 wherein the liquid medium contains carbohydrates, salt and water.

4. The process of claim 1 wherein the medium contains the lactic acid bacteria concentration of about $32 \times 10^6$ cfg/gram.

5. The process of claim 1 wherein the liquid medium is derived from adding water to lactic acid bacteria contained in a dry medium selected from pellets, tablets and powders.

6. The process of claim 3 wherein the carbohydrates are sugars at about 1.2% by weight.

7. The process of claim 1 wherein the weight amount of sprayed lactic acid bacteria medium is about 5% of the amount of waste material.

* * * * *